(12) United States Patent
Wilmering

(10) Patent No.: US 10,098,575 B2
(45) Date of Patent: Oct. 16, 2018

(54) METHODS AND SYSTEMS FOR DETERMINING PHYSIOLOGICAL INFORMATION BASED ON DISTORTION INFORMATION

(71) Applicant: Covidien LP, Mansfield, MA (US)

(72) Inventor: Tom Wilmering, Westminster, CO (US)

(73) Assignee: Covidien LP, Mansfield, MA (US)

( * ) Notice: Subject to any disclaimer, the term of this patent is extended or adjusted under 35 U.S.C. 154(b) by 826 days.

(21) Appl. No.: 14/604,601

(22) Filed: Jan. 23, 2015

(65) Prior Publication Data

US 2015/0201873 A1 Jul. 23, 2015

Related U.S. Application Data

(60) Provisional application No. 61/930,867, filed on Jan. 23, 2014.

(51) Int. Cl.
| | | |
|---|---|---|
| *A61B 5/1455* | (2006.01) | |
| *A61B 5/02* | (2006.01) | |
| *A61B 5/00* | (2006.01) | |
| *A61B 5/0295* | (2006.01) | |
| *A61B 5/024* | (2006.01) | |
| *A61B 5/021* | (2006.01) | |

(52) U.S. Cl.
CPC .......... *A61B 5/14551* (2013.01); *A61B 5/021* (2013.01); *A61B 5/0295* (2013.01); *A61B 5/02416* (2013.01); *A61B 5/7203* (2013.01)

(58) Field of Classification Search
CPC . A61B 5/1455; A61B 5/14551; A61B 5/0295; A61B 5/029; A61B 5/02416; A61B 5/7278; A61B 5/7203
See application file for complete search history.

(56) References Cited

U.S. PATENT DOCUMENTS

| | | | |
|---|---|---|---|
| 5,853,364 | A | 12/1998 | Baker, Jr. et al. |
| 6,157,850 | A | 12/2000 | Diab et al. |
| 6,334,065 | B1 * | 12/2001 | Al-Ali ................ A61B 5/14551 600/323 |
| 6,594,513 | B1 | 7/2003 | Jobsis et al. |
| 6,882,874 | B2 | 4/2005 | Huiku |
| 6,944,488 | B2 | 9/2005 | Roberts |
| 2011/0004081 | A1 | 1/2011 | Addison et al. |
| 2011/0028854 | A1 | 2/2011 | Addison et al. |
| 2011/0071406 | A1 | 3/2011 | Addison et al. |

OTHER PUBLICATIONS

Schuster, A., "Radiation Through a Foggy Atmosphere," Astrophysics Data System, Jan. 1905; 21:1-22.

(Continued)

*Primary Examiner* — Eric Winakur
(74) *Attorney, Agent, or Firm* — Shumaker & Sieffert, P.A.

(57) ABSTRACT

Methods and systems are provided for determining physiological information based on distortion factors and physiological signals. Physiological signals are received by a system. The system may receive or determine a value indicative of oxygen saturation. The distortion factors may be calculated based on the value indicative of oxygen saturation and the physiological signals. The distortion factors may be used to determine physiological information.

12 Claims, 6 Drawing Sheets

(56) References Cited

OTHER PUBLICATIONS

Bonner, R.F., Nossal R., Havlin, S., et al., "Model for Photon Migration in Turbid Biological Media," J. Opt. Soc. Am. A, Mar. 1987; 4: 423-432.
Patterson, Michael S., Chance, B., Wilson, B.C., "Time Resolved Reflectance and Transmittance for the Non-Invasive Measurement of Tissue Optical Properties," Applied Optics, Jun. 15, 1989; 28: 2331-2336.
Murray, W.B, and Foster, P.A., "The Peripheral Pulse Wave: Information Overlooked," J. Clin. Monit. vol. 12, No. 5, Sep. 1996, pp. 365-377.
Mannheimer, P.D., Fein, M.E., Casciani, J.R., "Physio-Optical Considerations in the Design of Fetal Pulse Oximetry Sensors," Eur. J. Obstet. Gynecol. Reprod. Biol., Mar. 1997; 72 Suppl: S9-19.
Kim, M.B., Ward, D.S., Cartwright, C.R., et al., "Estimation of Jugular Venous O2 Saturation from Cerebral Oximetry or Arterial O2 Saturation During Isocapnic Hypoxia," J. Clin. Monit. Comp., 2000; 16(3):191-9.
Mannheimer, P.D., "Simplified Path Length Model of Pulse Oximetry," 2003, No. 1 Focus Mul, Jahrgang 20, Marz, pp. 65-72.
Allen, J., "Photoplethysmography and its Application in Clinical Physiological Measurement," Physiol. Meas., vol. 28, pp. R1-R39, 2007.
Aoyagi, T., Fuse, Masayoshi, Kobayashi, N., et al., "Multiwavelength Pulse Oximetry: Theory for the Future," Anesth. Analg., Dec. 2007;105(6 Suppl):S53-58, tables of contents.
Shelly, Kirk H., "Photoplethysmography: Beyond the Calculation of Arterial Oxygen Saturation and Heart Rate," Anesth. Analg., vol. 105, pp. S31-S36, Dec. 2007.

\* cited by examiner ns to processing physiological signals, and more particularly relates to determining distortion factors based on a physiological signal and determining physiological information based on the distortion factors.

METHODS AND SYSTEMS FOR DETERMINING PHYSIOLOGICAL INFORMATION BASED ON DISTORTION INFORMATION

CROSS REFERENCE TO RELATED APPLICATION

This application claims the benefit of U.S. Provisional Application No. 61/930,867, filed Jan. 23, 2014, which is hereby incorporated by reference herein in its entirety.

SUMMARY

The present disclosure relates to processing physiological signals, and more particularly relates to determining distortion factors based on a physiological signal and determining physiological information based on the distortion factors.

Methods and systems are provided for determining distortion factors based on a received signal. In some embodiments, light signals are received by a system. The system may receive a value indicative of oxygen saturation. The distortion factors may be calculated based on the value indicative of oxygen saturation and the light signals. The distortion factors may be used to determine physiological information.

In some embodiments, a system for operating a physiological monitor includes an input configured for receiving a physiological signal, the signal comprising a first component corresponding to a first wavelength of light and a second component corresponding to a second wavelength of light. The system further includes one or more processors configured for receiving a value indicative of oxygen saturation. The one or more processors are further configured for determining a distortion factor corresponding to one of the first and second wavelengths of light based on the first component of the received physiological signal, the second component of the received physiological signal, and the value indicative of oxygen saturation. The one or more processors are further configured for determining physiological information based on the distortion factor.

In some embodiments, a method is provided for operating a physiological monitor. The method comprises receiving a physiological signal, the signal comprising a first component corresponding to a first wavelength of light and a second component corresponding to a second wavelength of light. The method further comprises receiving a value indicative of oxygen saturation. The method further comprises determining a distortion factor corresponding to one of the first and second wavelengths of light based on the first component of the received physiological signal, the second component of the received physiological signal, and the value indicative of oxygen saturation. The method further comprises determining physiological information based on the distortion factor.

In some embodiments, a system for operating a physiological monitor includes an input configured for receiving a physiological signal, the signal comprising a first component corresponding to a first wavelength of emitted light and a second component corresponding to a second wavelength of emitted light. The system further includes one or more processors configured for determining a value indicative of oxygen saturation based on a first assumption regarding the interaction of the emitted light and tissue of a subject and on the physiological signal. The one or more processors are further configured for determining a distortion factor corresponding to one of the first wavelength of emitted light and the second wavelength of emitted light based on a second assumption regarding the interaction of the emitted light and tissue of the subject, wherein the second assumption is based on the first assumption not being accurate, and on the physiological signal. The one or more processors are further configured for determining physiological information based on the distortion factor.

In some embodiments, a method is provided for operating a physiological monitor. The method comprises receiving a physiological signal, the signal comprising a first component corresponding to a first wavelength of emitted light and a second component corresponding to a second wavelength of emitted light. The method further comprises determining a value indicative of oxygen saturation based on a first assumption regarding the interaction of the emitted light and tissue of a subject and on the physiological signal. The method further comprises determining a distortion factor corresponding to one of the first wavelength of emitted light and the second wavelength of emitted light based on a second assumption regarding the interaction of the emitted light and tissue of the subject, wherein the second assumption is based on the first assumption not being accurate, and on the physiological signal. The method further comprises determining physiological information based on the distortion factor.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
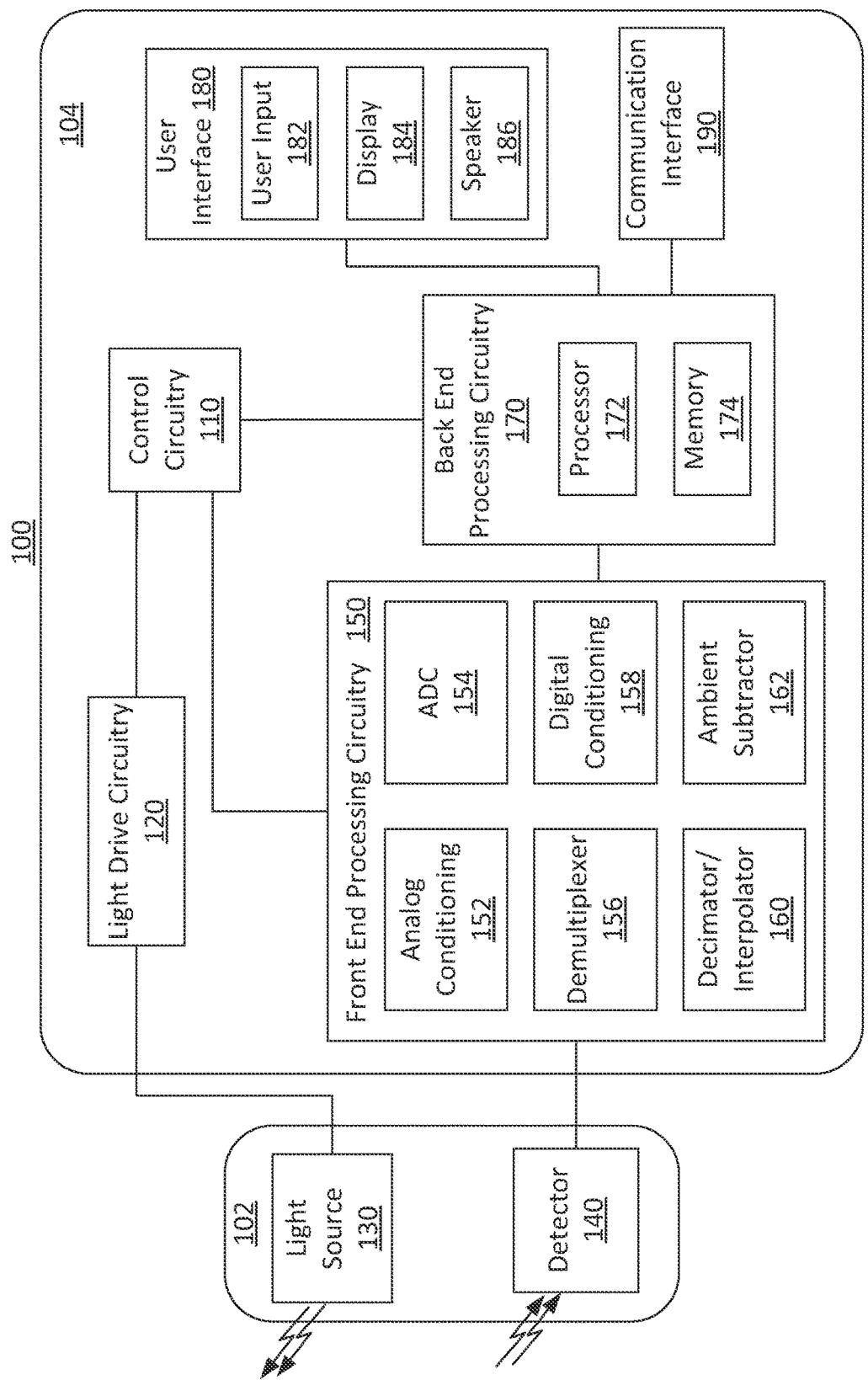
FIG. 1 shows a block diagram of an illustrative physiological monitoring system in accordance with some embodiments of the present disclosure.

The present disclosure is directed towards processing signals in a physiological monitoring system such as a medical device. In particular, a system is configured to determine distortion factors and determine physiological information based on the distortion factors.

A medical device such as a pulse oximeter may receive detected light signals. For example, a light signal may interact with a patient and then be detected using a photodetector. The amplitude and other features of the detected light signal may be used to determine physiological information. For example, physiological changes such as changes in path length or changes in the light absorbance may correspond to changes in the amplitude of the detected signal. These detected light signals are referred to herein as photoplethysmograph (PPG) signals.

In some embodiments, features of PPG signals are dominated by changes in arterial blood, such as changes in volume, due to the changing amount of arterial blood within the tissue over the cardiac cycle. The relative pulse amplitude of PPG signals corresponding to different wavelengths of light provide information about the oxygenation of arterial blood, and thus allows for the calculation of arterial oxygen saturation, $SpO_2$.

As is understood in the art, there are several fundamental challenges involved in the use of optical tissue interrogation to determine physiological information. One challenge involved in optical tissue interrogation is the unknown light loss between a sensor and the skin of the subject. This loss is variable and may be due in part to sensor construction, clinician practice in placement of the sensor, and differences in the physical site of the interrogation. Furthermore, the background scattering and absorption, which is convolved with the signal of interest, is unknown, variable between subjects, and can even change within a single subject during the course of monitoring.

Another challenge involved in optical tissue interrogation is the variability in the emitters typically used. While LEDs are low cost and generally effective as emitters, they exhibit variability, both between different emitters and in the spectrum emitted by any individual LED.

Yet another challenge involved in optical tissue interrogation is that the average path length through the medium, which is included in calculations using absorbed and scattered light, is dependent on a number of variable factors, including the absorption, the scattering, and the specific wavelength of light. Accordingly, the change in path length creates variability in measures determined from optically interrogated tissue.

In view of these and other challenges, the use of optical tissue interrogation to calculate physiological parameters typically relies on a number of simplifying assumptions. Accordingly, the resulting calculations can only be considered approximations of the relevant parameters. In some cases, such as with cerebral oximetry, the saturation value received may only be treated as an evaluation of a deviation from a baseline saturation value, which has clinical utility, but does not provide an actual measure of saturation. In other cases, for example in pulse oximetry, while the arterial oxygen saturation or $SpO_2$ value is neither a fractional nor functional measure of saturation, it has been found that the value has good fidelity to the actual saturation value in the blood, due at least in part to the fact that the simplifying assumptions are close to true for the light signals typically involved in pulse oximetry.

The aforementioned scattering and absorption variability involved in the optical interrogation of tissue may be thought of as factors that distort the simplified view of optical tissue interrogation. The unpredictability and variability that distorts the view so as to prevent an accurate understanding of the physiology may be considered to be analogous to an atmosphere with fine particles of matter that causes such an appreciable amount of scattering so as to be considered "foggy." In some embodiments, a known or approximated physiological parameter, such as arterial oxygen saturation, can be used to solve for one or more of the factors that distort the simplified view of optical tissue interrogation. It will be understood that the distortion factors provide additional information about the interaction of the emitted light and the tissue of the subject that may not be taken into account in calculations relying on simplifying assumptions. This additional information may be used to improve the calculations of physiological parameters and may also be used to determine additional physiological information. For example, the distortion factors may be used for further evaluation of the original assumptions and to otherwise monitor the accuracy of the resulting approximation. Furthermore, the distortion factors may be used to determine other related physiological parameters with improved accuracy.

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Pulse oximeters may be included in patient monitoring systems that measure and display various blood flow characteristics including, but not limited to, the blood oxygen saturation (e.g., arterial, venous, or both). Such patient monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), systemic vascular resistance, mean arterial pressure, cardiac output, central venous pressure, oxygen demand, adaptive filter parameters, any other suitable physiological parameters, or any combination thereof. Exemplary embodiments of determining respiration rate are disclosed in Addison et al. U.S. Patent Publication No. 2011/0071406, published Mar. 24, 2011, which is hereby incorporated by reference herein in its entirety. Exemplary embodiments of determining respiration effort are disclosed in Addison et al. U.S. Patent Publication No. 2011/0004081, published Jan. 6, 2011, which is hereby incorporated by reference herein in its entirety. Exemplary embodiments of determining blood pressure are disclosed in Addison et al. U.S. Patent Publication No. 2011/0028854, published Feb. 3, 2011, which is hereby incorporated by reference herein in its entirety.

Pulse oximetry may be implemented using a photoplethysmograph. Pulse oximeters and other photoplethysmograph devices may also be used to determine other physiological parameter and information as disclosed in: J. Allen, "Photoplethysmography and its application in clinical physiological measurement," *Physiol. Meas.*, vol. 28, pp. R1-R39, March 2007; W. B. Murray and P. A. Foster, "The peripheral pulse wave: information overlooked," *J. Clin. Monit.*, vol. 12, pp. 365-377, September 1996; and K. H. Shelley, "Photoplethysmography: beyond the calculation of arterial oxygen saturation and heart rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, and locations with strong pulsatile arterial flow. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. As another example, the system may determine regional blood oxygen saturation using two wavelengths of light and two detectors located at different distances from the emitters. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, a light drive modulation may be used. For example, a first light source may be turned on for a first drive pulse, followed by an off period, followed by a second light source for a second drive pulse, followed by an off period. The first and second drive pulses may be used to determine physiological parameters. The off periods may be used to detect ambient signal levels, reduce overlap of the light drive pulses, allow time for light sources to stabilize, allow time for detected light signals to stabilize or settle, reduce heating effects, reduce power consumption, for any other suitable reason, or any combination thereof.

It will be understood that the techniques described herein are not limited to pulse oximeters and may be applied to any suitable physiological monitoring device.

The following description and accompanying FIGS. 1-6 provide additional details and features of some embodiments of the present disclosure.

FIG. 1 shows a block diagram of illustrative physiological monitoring system 100 in accordance with some embodiments of the present disclosure. System 100 may include a sensor 102 and a monitor 104 for generating and processing sensor signals that include physiological information of a subject. In some embodiments, sensor 102 and monitor 104 may be part of an oximeter. In some embodiments, system 100 may include more than one sensor 102.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the red and IR wavelengths in the subject's tissue). In some embodiments, the detection signal may be preprocessed by sensor 102 before being transmitted to monitor 104. Although only one detector 140 is depicted in FIG. 1, in some embodiments, sensor 102 may include additional detectors located at different distances from the light source 130. In embodiments with additional detectors, the sensitivity of the additional detectors may vary based on the distance between the detector and light source 130 such that a far detector may be more sensitive to light than a near detector.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102 using, for example, one or more inputs.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

In some embodiments, control circuitry 110 and light drive circuitry 120 may generate light drive parameters based on a metric. For example, back end processing 170 may receive information about received light signals, determine light drive parameters based on that information, and send corresponding information to control circuitry 110.

Figure 2A:
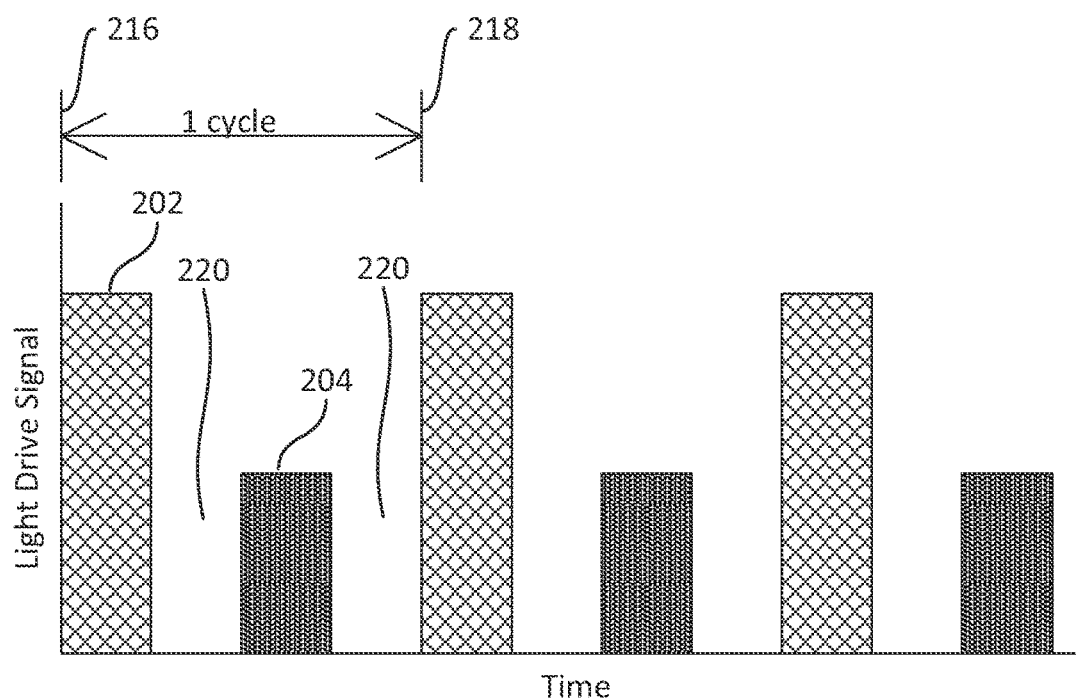
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. Light drive pulses 202 and 204 are illustrated as square waves. These pulses may include shaped waveforms rather than a square wave. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a shaped pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130. Red light drive pulse 202 may have a higher amplitude than IR light drive pulse 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate sensor signals that include physiological information that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive a detection signal from detector 140 and provide one or more processed signals to back end processing circuitry 170. In some embodiments, front end processing circuitry 150 may receive the detection signals from one or more inputs of monitor 104. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
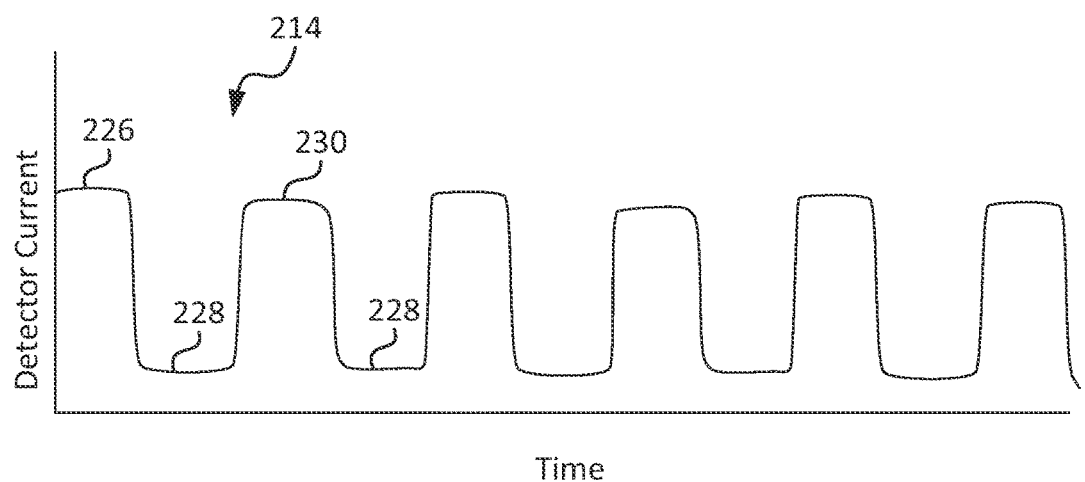
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valleys 228 of detector current waveform 214 may be synchronous with periods of time during which no light is being emitted by the light source, or the light source is returning to dark, such as "off" periods 220. While no light is being emitted by a light source during the valleys, detector current waveform 214 may not fall all of the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive a one or more detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valleys 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 228 that occurs immediately after the IR component 230). Demultiplexer 156 may operate under the control of control circuitry 110. For example, demultiplexer 156 may use timing control signals from control circuitry 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal or signals.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal, by analog conditioning 152 to map the expected range of the signal to the full or close to full output range of analog-to-digital converter 154. The output value of analog-to-digital converter 154, as a function of the total analog gain applied to the detection signal, may be given as:

$$\text{ADC Value} = \text{Total Analog Gain} \times [\text{Ambient Light} + \text{LED Light}]$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may results in fewer bits of resolution for the portion of the signal from the light source. This may have a detrimental effect on the signal-to-noise ratio of the detection signal. Accordingly, passive or active filtering or signal modification techniques may be employed to reduce the effect of ambient light on the detection signal that is applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further process sensor signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of a venous signal, a blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Processor 172 may further compute one or more distortion factors based on the received physiological signals, and the calculated physiological information. In some embodiments, one or more distortion factors may be used to improve the accuracy of the calculation of any of the above-mentioned or other suitable physiological parameters, may be used to calculate additional physiological information, may be used for any other suitable purpose, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store calculated values, such as pulse rate, blood pressure, blood oxygen saturation, fiducial point locations or characteristics, initialization parameters, systemic vascular resistance, mean arterial pressure, cardiac output, central venous pressure, oxygen demand, adaptive filter parameters, distortion factors, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's blood oxygen saturation generated by monitor 104 (e.g., an "$SpO_2$" or a regional oximetry measurement), pulse rate information, respiration rate and/or effort information, blood pressure information, hemoglobin concentration information, systemic vascular resistance, mean arterial pressure, cardiac output, central venous pressure, oxygen demand, any other parameters, and any combination thereof. Display 184 may include any type of display such as a cathode ray tube display, a flat panel display such as a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, inputs, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In addition, while a single processor is depicted in FIG. 1, it will be understood that one or more processors may be used to perform the functionality described above. In other embodiments, the functionality of one or more of the components may be performed in a different order or may not be required. In an embodiment, all of the components of physiological monitoring system 100 can be realized in processor circuitry.

Figure 3:
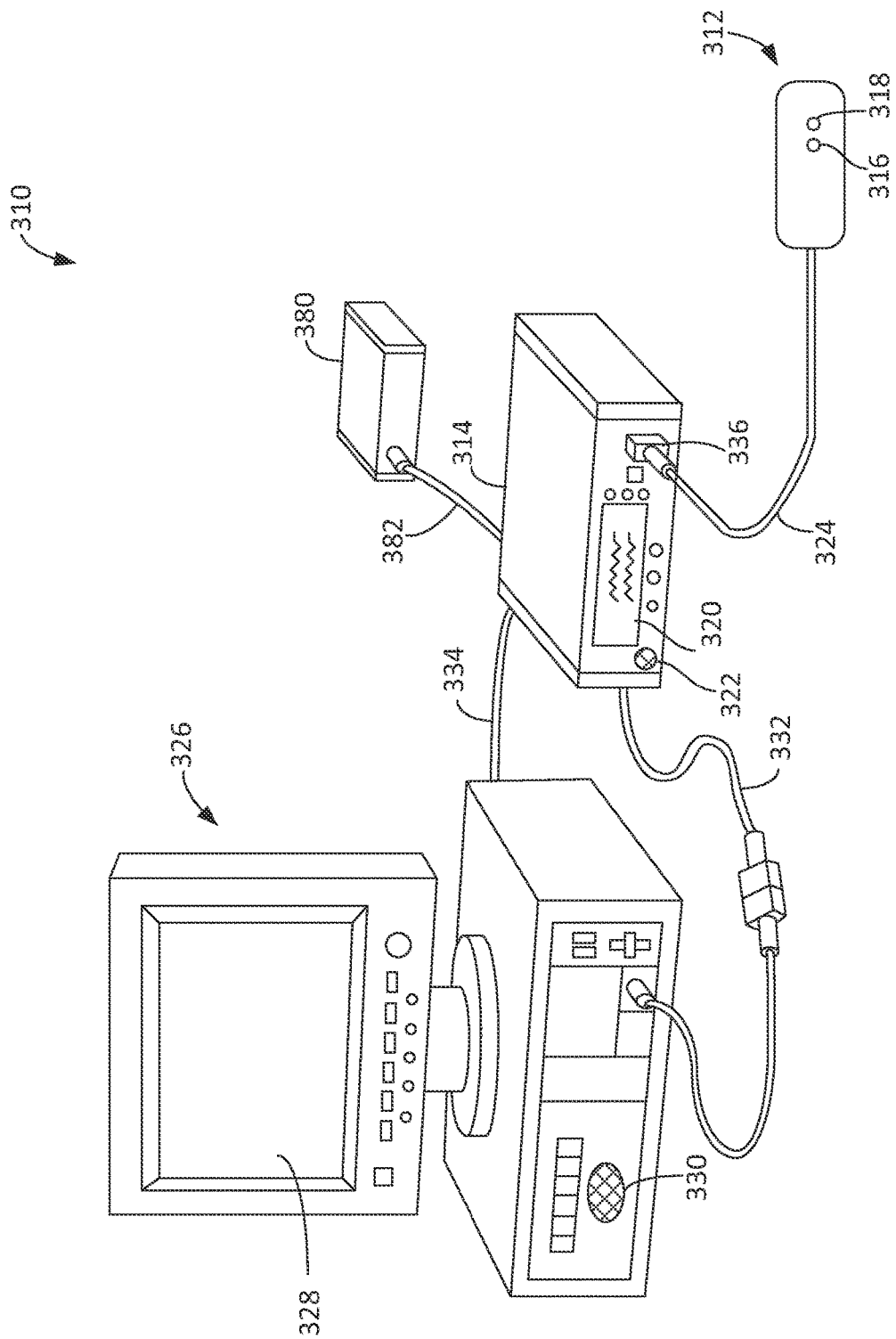
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body. In an example, an oximeter sensor may be located at a first position and a thermodilution sensor may be located at a second location. In another example, an oximeter sensor and a temperature sensor may be located near to one another or in the same structure.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and light detection received from one or more sensor units such as sensor unit 312. For example, monitor 314 may be configured to determine pulse rate, respiration rate, respiration effort, blood pressure, blood oxygen saturation (e.g., arterial, venous, regional, or a combination thereof), hemoglobin concentration (e.g., oxygenated, deoxygenated, and/or total), systemic vascular resistance, mean arterial pressure, cardiac output, central venous pressure, oxygen demand, any other suitable physiological parameters, or any combination thereof. Monitor 314 may also be configured to determine distortion factors and determine any of the above-mentioned or other suitable physiological parameters based thereon. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324 at port 336. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326, may be referred to collectively as processing equipment. For example, processing equipment may be configured to amplify, filter, sample and digitize an input signal from sensor 102 or 312 (e.g., using an analog-to-digital converter), and calculate physiological information from the digitized signal. Processing equipment may be configured to generate light drive signals, amplify, filter, sample and digitize detector signals, sample and digitize other analog signals, calculate physiological information from the digitized signal, perform any other suitable processing, or any combination thereof. The processing equipment may include one or more processors. In some embodiments, all or some of the components of the processing equipment may be referred to as a processing module.

Figure 4:
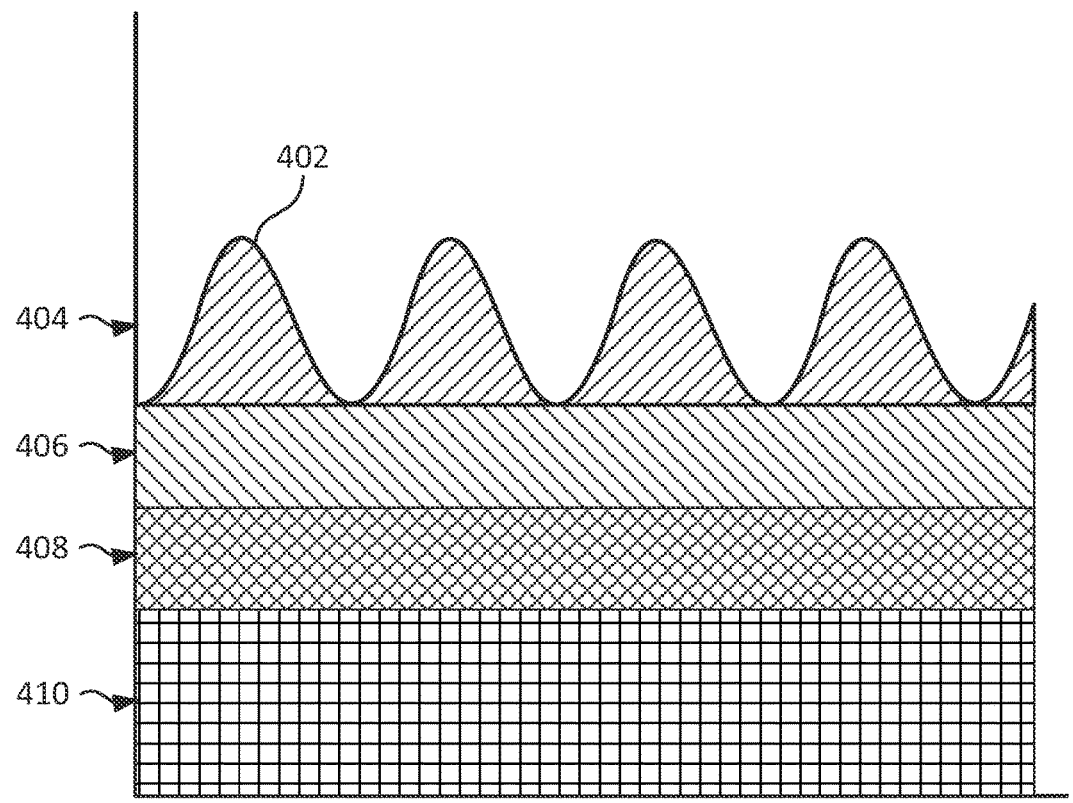
FIG. 4 shows an illustrative plot of a physiological signal in accordance with some embodiments of the present disclosure.

FIG. 4 shows an illustrative plot 400 of physiological signal 402 in accordance with some embodiments of the present disclosure. In some embodiments, physiological signal 402 may be considered to include an AC component and one or more DC components. It will be understood that physiological signal 402 is shown to illustrate the usage of the DC and AC signal terminology used herein. It will also be understood that AC and DC terms need not refer to the traditional electrical power definitions. Rather, DC may refer to the portion of the signal that is relatively constant over time, while AC may refer to the portion of the signal that changes over time. For example, the AC component may vary substantially with a cardiac cycle. In the illustrated example, shaded region 404 may correspond to the AC signal component of physiological signal 402, and shaded regions 406, 408, and 410 may collectively correspond to the total DC signal component of physiological signal 402. It will be understood that the particular division of AC and DC components shown in plot 400 is merely exemplary and that any suitable division may be used. For example, in some embodiments the DC level may be identified at an initial point and remain constant for a predefined interval. In another example, the DC level may track the lowest point of the AC oscillation and be updated at regular intervals such as every pulse, every $10^{th}$ pulse, every 10 seconds, or any other suitable interval. In some embodiments, the interval may vary based on parameters such as patient condition. In some embodiments, the DC component of a received PPG signal may correspond to the amount of light received at diastole, and the AC component may correspond to the variations above the diastole level.

The following mathematical expressions (1)-(11) provide an exemplary derivation of distortion factors associated with the calculation of arterial oxygen saturation.

By way of background, approximately 98-99% of all the oxygen carried in our blood is bound to hemoglobin, while the remaining fraction is dissolved in the plasma. Because the binding of oxygen molecules in hemoglobin is cooperative, individual hemoglobin molecules in the blood are generally found with either all four binding sites occupied by oxygen molecules or none occupied. Fully saturated blood is comprised of only the fully bound molecules, referred to as oxyhemoglobin, or O2Hb, while desaturated blood includes a mixture of O2Hb and fully deoxygenated molecules, referred to as deoxyhemoglobin, or HHb. The blood's functional oxygen saturation is thus defined as the relevant amount of oxygenated hemoglobin to the total amount of hemoglobin capable of delivering oxygen, or:

$$sO_2 \equiv \frac{cO_2Hb}{cO_2Hb + cHHb} \quad (1)$$

where $cO_2Hb$ and $cHHb$ refer to the concentrations of oxyhemoglobin and deoxyhemoglobin molecules in the blood.

In some embodiments, a related calculation of an arterial oxygen saturation value, $SpO_2$, may be determined by determining a ratio-of-ratios value. The following mathematical expressions provide an exemplary derivation of the ratio-of-ratios equation. The starting point is the classic Lambert-Beer law, which describes the attenuation of light as it passes through a colored solution as the sum of the effects coming from each of the individual absorbers:

$$A \equiv -\log\left(\frac{I_{out}}{I_{in}}\right) = \ell \cdot \sum_i (\beta_i \cdot cX_i) \quad (2)$$

where A is the absorbance or total light loss, $I_{in}$ and $I_{out}$ refer to the incident and transmitted light intensities, l is the path length through the medium, and $\beta_i$ and $cX_i$ are the spectral absorption characteristics and concentration of each of the $i^{th}$ substances in the medium. In highly scattering media such as tissue, however, the path length is not simply the linear thickness of the tissue as in the classic case. Instead, the distance traveled by the light is a complex function of both the scattering and absorption of the medium. To account for these effects, a simplifying assumption is made by replacing l with $\bar{l}$, which denotes an "effective mean path length" of detected light accounting for all of the effects of scattering into a single term, giving the following Modified Lambert-Beer law equation:

$$A \equiv -\log\left(\frac{I_{out}}{I_{in}}\right) = \bar{l} \cdot \sum_i (\beta_i \cdot cX_i) \quad (3)$$

The absorbers of light within the tissue include O2Hb, HHb, and additional absorbers such as the venous blood, bone, skin, and tendons. To cancel the light loss attributed to these additional absorbers, another simplifying assumption is made. Specifically, it is assumed that only the amount of arterial blood in the tissue changes for a given change in time within the cardiac cycle. Based on this assumption, any change in light intensity is entirely attributable to the change in the amount of arterial blood in the tissue at these two points in time. This assumption can be further understood with reference to FIG. 4, for example. In essence, the assumption is that shaded portion 404 corresponds to changes in arterial blood volume, and the remaining shaded portions 406, 408, and 410 correspond to any or all of the venous blood, static arterial blood, the bone, the skin, the tendons and other tissue. Assuming this is true, light loss coming from these additional absorbers can be cancelled by taking the difference of the measurements at two points in time within the cardiac cycle, which results in the following expression:

$$A(t_1)-A(t_2)-\log(I_{out}(t_2))-\log(I_{out}(t_1))= \bar{l}\cdot\beta_a(cHb_a(t_1)-cHb_a(t_2)) \quad (4)$$

where $t_1$ and $t_2$ are the two points in time, and $\beta_a$ and $cHb_a$ refer to the absorption characteristic and concentration of arterial hemoglobin in the tissue. By expanding $\beta_a$ to an equivalent form in terms of the combination of the absorption characteristics $\beta_{O_2Hb}$ and $\beta_{HHb}$ for O2Hb and HHb, respectively, and the saturation value S from Eq. (1) above, Eq. (4) becomes:

$$A(t_1)-A(t_2)-\log(I_{out}(t_2))- \bar{l}\cdot(S\beta_{O_2Hb}+(1-S)\beta_{HHb})\cdot\Delta cHb_a \quad (5)$$

where $\Delta cHb_a$ is used to indicate the change in tissue arterial hemoglobin concentration over the time increment.

Conventional pulse oximeters typically perform the measurement indicated in the middle portion of Eq. (5) for two wavelengths $\lambda_1$, $\lambda_2$ and calculate the ratio-of-ratios term R as:

$$R = \frac{(\log(I_{out}(t_2)) - \log(I_{out}(t_1)))_{\lambda_1}}{(\log(I_{out}(t_2)) - \log(I_{out}(t_1)))_{\lambda_2}} \quad (6a)$$

Applying the same ratio to the right side of Eq. (5) provides the following equation:

$$R = \frac{(S\beta_{O_2Hb}^{\lambda_1} + (1-S)\beta_{HHb}^{\lambda_1}) \cdot \Delta cHb_a^{\lambda_1} \cdot \bar{l}_{\lambda_1}}{(S\beta_{O_2Hb}^{\lambda_2} + (1-S)\beta_{HHb}^{\lambda_2}) \cdot \Delta cHb_a^{\lambda_2} \cdot \bar{l}_{\lambda_2}} \quad (6b)$$

If the right hand terms of Eq. (6b) are grouped into a single value $\Omega$, solving for S results in the saturation estimate:

$$\Omega = \frac{\Delta cHb_a^{\lambda_1} \cdot \bar{l}_{\lambda_1}}{\Delta cHb_a^{\lambda_2} \cdot \bar{l}_{\lambda_2}} \quad (7)$$

$$SpO_2 = \frac{\beta_{HHb}^{\lambda_1} - R \cdot \Omega^{-1} \cdot \beta_{HHb}^{\lambda_2}}{R \cdot \Omega^{-1} \cdot (\beta_{O_2Hb}^{\lambda_2} - \beta_{HHb}^{\lambda_2}) + \beta_{HHb}^{\lambda_1} - \beta_{O_2Hb}^{\lambda_1}} \quad (8)$$

For the purposes of determining $SpO_2$, yet another simplifying assumption is made. Here, it is assumed that both wavelengths of light pass through the same modulating arterial blood volumes with equal path lengths, such that $\Omega$ equates to unity. Accordingly, a value can be calculated that approximates the arterial saturation of oxygen.

As described above, a number of simplifying assumptions are made in order to derive and calculate $SpO_2$. First, a broadly defined "effective mean path length" was used to replace the length term in the original Lambert-Beer equation in order to attempt to account for the complex function of both the scattering and absorption of light through the tissue. Next, it was assumed that arterial blood accounted for all changes in light intensity for a given change in time within the cardiac cycle to allow us to cancel out effects of other tissue. Finally, it was assumed that the two wavelengths of light pass through the same modulating arterial blood volumes with equal path lengths in order to cancel the path length and the change in tissue arterial hemoglobin concentration terms.

In spite of these simplifying assumptions, the $SpO_2$ value yielded by conventional pulse oximetry methods as derived above has been observed as a reasonably accurate value and has provided significant clinical value in practice. In accordance with the present disclosure, the reasonably accurate $SpO_2$ value and the previously described equations can be used to resolve the aforementioned coupling, background scattering and absorption, LED variability, and path length variability issues. Specifically, we can start at Eq. (4) above and replace $A(t_1)-A(t_2)$ with $\Delta A_{\lambda_i}$ and $cHb_a(t_1)-cHb_a(t_2)$ with $\Delta c_{HB_a,\lambda_i}$ for ease of reference, resulting in:

$$\Delta A_{\lambda_i} = \bar{l}_{\lambda_i} \cdot \Delta c_{HB_a,\lambda_i} \cdot (S \cdot \beta_{O_2HB,\lambda_i} + (1-S)\beta_{HHB,\lambda_i}) \quad (9)$$

where $$\Delta A_{\lambda_i} = \log(I_{out_{t2,\lambda_i}}) - \log(I_{out_{t1,\lambda_i}}), \Delta c_{HB_a,\lambda_i}$$

is the change in tissue arterial hemoglobin concentration over a time increment for a given wavelength, $\lambda_i$, and S is the $SpO_2$ value from a conventional approach, such as the one detailed above. In Eq. (9), it can be seen that the variability issues related to scattering, absorption, and path length may be resolved by the term $\bar{l}_{\lambda_i} \cdot \Delta c_{HB_a,\lambda_i}$ since these were the terms that were previously assumed to cancel out due to the simplification used to calculate $SpO_2$. Thus, it may be helpful to define this term as distortion factor $W_{dis,\lambda_i}$, which reduces Eq. (9) to:

$$\Delta A_{\lambda_i} = W_{dis,\lambda_i} \cdot (S \cdot \beta_{O_2HB,\lambda_i} + (1-S)\beta_{HHB,\lambda_i}) \quad (10)$$

Where $\beta_{O_2HB,\lambda_i}$ and $\beta_{HHBA,\lambda_i}$ are the absorption characteristics at the specific values for the individual emitters (e.g., as measured when the emitters were manufactured). Accordingly, applying this equation to a pulse oximetry device using red and IR wavelengths as an example, the following linear algebra matrix may result:

$$\begin{bmatrix} \Delta A_{\lambda_{red}} \\ \Delta A_{\lambda_{IR}} \end{bmatrix} = \begin{bmatrix} W_{dis,\lambda_{red}} \\ W_{dis,\lambda_{IR}} \end{bmatrix} \cdot \left[ S \cdot \begin{bmatrix} \beta_{O_2HB,\lambda_{red}} \\ \alpha_{O_2HB,\lambda_{IR}} \end{bmatrix} + (1-S) \cdot \begin{bmatrix} \beta_{HHB,\lambda_{red}} \\ \beta_{HHB,\lambda_{IR}} \end{bmatrix} \right] \quad (11)$$

Since the values of $\Delta A_{\lambda_{red}}$, $\Delta A_{\lambda_{IR}}$, S, $\beta_{HBO_2,\lambda_{red}}$, $\beta_{HBO_2,\lambda_{IR}}$, $\beta_{HHB,\lambda_{red}}$, and $\beta_{HHB,\lambda_{IR}}$ are known, the two values of $W_{dis}$ can be solved directly. As will be described in further detail below, these distortion factors can be used with the same sensor setup and corresponding vasculature combination to improve the calculation of physiological parameters and/or to determine additional physiological information. It will be appreciated that although only two wavelengths were referred to in the example above, the pulse oximeter or other device may use additional wavelengths and thus could solve for additional values of $W_{dis}$.

It will be understood that distortion factors, as calculated in accordance with the present disclosure, may be used for a number of purposes, as will be described in detail below. In some embodiments, distortion factors may be used to determine physiological information. For example, distortion factors may be used to calculate or approximate physiological parameters or indices. In some embodiments, distortion factors may be used to improve methods for calculating physiological parameters or indices. In some embodiments, distortion factors themselves may be monitored to determine confidence information associated with the physiological signals employed in the present disclosure.

In some embodiments, a value indicative of local blood perfusion may be determined based on a calculated distortion factor. As used herein, blood perfusion generally refers to the flow of blood to a given amount of tissue. Current methods of assessing the quality of local perfusion using pulse oximetry typically rely on calculation of percent modulation. Percent modulation is typically a ratio of the AC component of an IR signal to the baseline, or DC component, of the IR signal. While the percent modulation generally provides a measure of signal strength and provides some information regarding perfusion quality, it is convolved with many of the confounding factors discussed above because it effectively is only measuring the change in light intensity. Given that the distortion factors capture many of these same confounding factors, it will be understood that in some embodiments, an improved value indicative of blood perfusion may be determined by multiplying the percent modulation ratio for a given wavelength by the inverse of the corresponding distortion factor. In some embodiments, the value indicative of local perfusion may be calculated according to the following expression:

$$\frac{AC_{\lambda_{IR}}}{DC_{\lambda_{IR}}} \cdot \frac{1}{W_{dis,\lambda_{IR}}} \quad (12)$$

Such a calculation will result in a perfusion index that more accurately represents the true change in fluid alone, since the distortion factor cancels out many of the confounding factors. In some embodiments, the perfusion index may be monitored continuously, periodically, or on demand. In some embodiments, the perfusion index may be displayed on a display, such as display 184 of FIG. 1. The perfusion index may be displayed in any suitable form, such as a number, a trace, or a bar display. In some embodiments, the perfusion index may be monitored in order to provide an alarm if the perfusion index is too low or too high. For example, the perfusion index may be compared to one or more thresholds and an alarm may be generated based on the comparison (e.g., when the perfusion index crosses a threshold). The alarm may be an audible alarm, a visual alarm, or a combination thereof.

In some embodiments, the perfusion index may be used to determine information about additional physiological parameters. Because perfusion relates to the flow of blood, the perfusion index, calculated based on a distortion factor, can be used to determine flow information, such as cardiac output and stroke volume. As used herein, cardiac output generally refers to the volume of blood pumped by the heart. In some embodiments, perfusion may be correlated to cardiac output. Therefore, changes in perfusion can be correlated to changes in cardiac output. In some embodiments, a relative change in perfusion can be correlated to a relative change in cardiac output. In some embodiments, cardiac output can be determined based on perfusion and calibration information. For example, a known reading of cardiac output can be used to generate the calibration information. Once calibrated, cardiac output can be determined based on the perfusion index. In some embodiments, the calibration information may be updated periodically.

In some embodiments, cardiac output may be considered to be proportional to the product of heart rate and the perfusion index, as shown by the following equation:

$$\text{Cardiac Output} \propto \text{Heart Rate} \times \frac{AC_{\lambda_{IR}}}{DC_{\lambda_{IR}}} \cdot \frac{1}{W_{dis,\lambda_{IR}}} \quad (13)$$

With a known cardiac output, heart rate, and perfusion index, it is possible to solve Eq. 13 for the proportional relationship between cardiac output and the product of heart rate and the perfusion index. Once calibrated, Eq. 13 may be used to calculate and display cardiac output, for example, continuously, periodically, or on demand. In some embodiments, an index can be calculated to simply track changes in "implied cardiac output" from a baseline, which would not require a known value of cardiac output.

As used herein, stroke volume generally refers to the volume of blood pumped by the heart during each cycle. Cardiac output and stroke volume are related based on the following expression:

$$\text{Cardiac Output} = \text{Stroke Volume} \cdot \text{Heart Rate} \quad (14)$$

Accordingly, the stroke volume may be determined based on cardiac output and heart rate. Thus, for the reasons discussed above, perfusion may also be correlated to stroke volume. In some embodiments, a relative change in perfusion can be correlated to a relative change in stroke volume. In some embodiments, stroke volume can be determined based on perfusion, heart rate, and calibration information. For example, a known reading of cardiac output and a known heart rate can be used to generate the calibration information. Once calibrated, stroke volume can be determined based on the perfusion index and heart rate. In some embodiments, the calibration information may be updated periodically. In some embodiments, when perfusion is calculated on a pulse-by-pulse basis, heart rate information is not needed.

In some embodiments, the calculation of cardiac output and stroke volume may also take into account changes in oxygen saturation. When oxygen saturation changes, the AC and DC components in the perfusion equation may change, for example, due to changes in the attenuation of the blood and not due to changes in perfusion. Accordingly, the calculation of cardiac output and stroke volume may be based on oxygen saturation or changes in oxygen saturation.

In some embodiments, other physiological parameters may be determined based on one or more distortion factors. For example, the concept of distortion factors may be applied to improve the accuracy of the calculation of regional oxygen saturation ($rSO_2$) of tissue. Although there are currently systems with sensors and methods that calculate $rSO_2$, the resulting calculations may not be precise measures of saturation of tissue under the sensors and instead may be rough estimations that are helpful to determine deviation from a baseline saturation. As will be described below, the distortion factors determined, for example, based on an accurate arterial saturation value $SpO_2$ can be applied to improve the calculation of $rSO_2$.

Figure 5A:
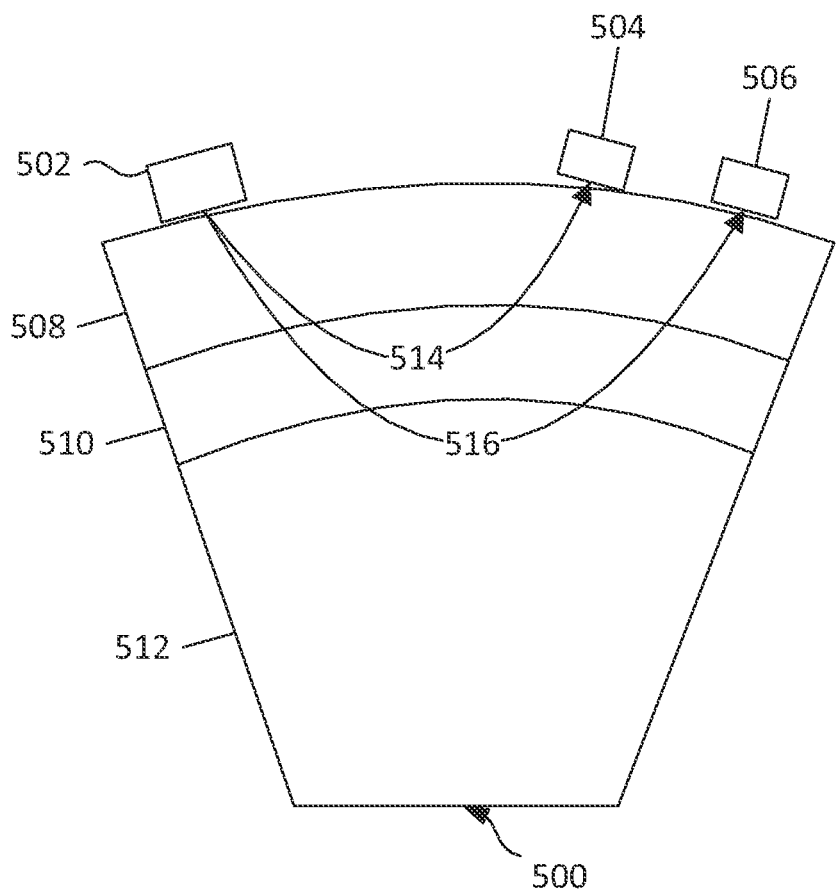
FIG. 5A shows an illustrative schematic of a cross section of a light source and two detectors applied to the forehead of a subject in accordance with some embodiments of the present disclosure.
Figure 5B:
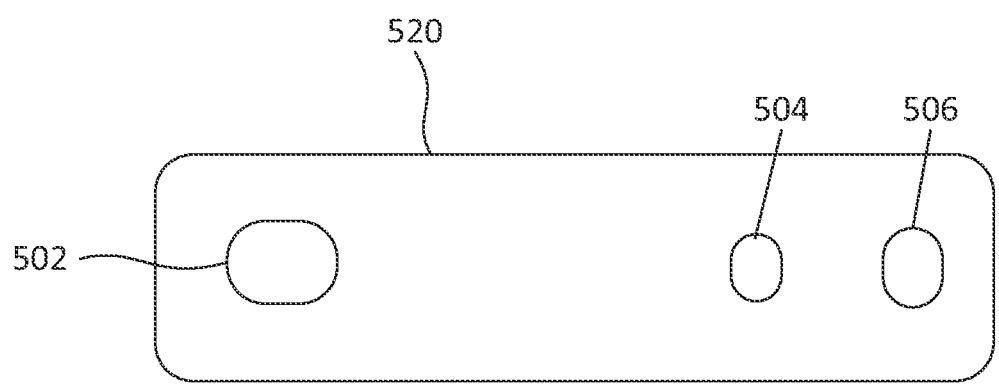
FIG. 5B shows a plan view of the bottom of a sensor unit incorporating a light source and two detectors in accordance with some embodiments of the present disclosure.

Embodiments for calculating $rSO_2$ will be described with reference to FIGS. 5A and 5B in order to illustrate the use of distortion factors to improve the calculation of $rSO_2$ in accordance with the present disclosure. FIG. 5A shows an illustrative schematic where a light source 502 and detectors 504 and 506 are shown in relation to a cross section of the subject's forehead 500. Cross section 500, as illustrated herein, comprises a number of layers, including layer 508 which may be comprised of the subject's skull, scalp, skin, and related tissue, layer 510 which may be comprised of the subject's cerebral spinal fluid, and layer 512, which may be comprised of the subject's brain and other tissue. FIG. 5B shows a plan view of the bottom of single sensor unit 520 that may incorporate light source 502 and detectors 504 and 506. Light source 502 may generally be configured to emit light at particular wavelengths with any of the capabilities discussed with respect to the light sources described above with reference to FIGS. 1 and 3. Similarly, detectors 504 and 506 may generally be configured to detect intensities of light with any of the capabilities discussed with respect to the detectors described above with reference to FIGS. 1 and 3. Sensor unit 520 may be connected to any combination of processing equipment as described above with respect to FIGS. 1 and 3. Detectors 504 and 506 may be placed at known and fixed distances from light source 502. The difference in distances from light source 502 results in different depths of penetration of the light measured at each of detectors 504 and 506. These different depths are illustrated by the simplified mean optical paths 514 and 516. As shown in FIG. 5A, light traveling from light source 502 to detector 506 may penetrate deeper beneath the skin than light traveling from light source 502 to detector 504.

In some embodiments of calculating $rSO_2$, light source 502 emits light at two separate wavelengths, and the intensity of the light at each of these wavelengths is measured at both detectors 504 and 506. As noted above, light measured at detector 504 corresponds to a shallow penetration, and light measured at detector 506 corresponds to a deep penetration. In some embodiments of calculating $rSO_2$, the difference between the deep and shallow penetrations is correlated to the saturation of the region of tissue of interest using the Modified Lambert-Beer approach. Although the resulting $rSO_2$ calculations have some clinical value, they may be distorted by the same scattering and absorption variability as discussed above, such that they do not provide a precise measure of the saturation of the tissue of interest.

Accordingly, distortion factors may be used to capture this variability and improve the calculation of $rSO_2$. As will be described in more detail below, in some embodiments, a known $SpO_2$ value can be used to determine one or more distortion factors which will in turn allow for an improved calculation of $rSO_2$. The resulting $rSO_2$ value will be improved because it accounts for the variability in scattering and absorption. Embodiments for an improved calculation of $rSO_2$ using distortion factors will be described in further detail with reference to FIGS. 5A and 5B and mathematical expressions (15)-(20) below.

In some embodiments, the assumption is made that the signal representing the shallow penetration, e.g., the signal measured by detector 504 of FIG. 5A, is dominated by arterial blood, since the light detected may pass through layers predominantly consisting of arterial blood. Given this assumption, the known $SpO_2$ value, which is a measure of arterial oxygen saturation, can be related to distortion factors associated with the shallow penetration by use of the Lambert-Beer equations. While the arterial component of signals in pulse oximetry described above were perceived as changing in time due to the influence of the pulse, the signals measured in the calculation of regional oxygen saturation may not be as influenced by the pulse, and thus may be considered to remain constant over time. Accordingly, rather than the Lambert-Beer equations above which refer to the change in absorption, $\Delta A$, the absorption $A$ can be expressed as the classic Lambert-Beer value as follows:

$$A = -\log\left(\frac{I_{out}}{I_{in}}\right) \quad (15)$$

Applying the same general principles above to relate the absorption $A$ to all components of the path length, $A$ can be described generally in terms of $SpO_2$, the distortion factors $W_{dis}$, and known $\beta_{HBO_2}$ and $\beta_{HHB}$ coefficients for any number of emitted wavelengths of light $(\lambda_1, \lambda_2, \lambda_3, \ldots \lambda_i)$ as follows:

$$\begin{bmatrix} A_{\lambda_1} \\ \cdot \\ \cdot \\ \cdot \\ A_{\lambda_i} \end{bmatrix} = \begin{bmatrix} W_{dis,\lambda_1} \\ \cdot \\ \cdot \\ \cdot \\ W_{dis,\lambda_i} \end{bmatrix} \left[ SpO_2 \cdot \begin{bmatrix} \beta_{O_2HB,\lambda_1} \\ \cdot \\ \cdot \\ \beta_{O_2HB,\lambda_i} \end{bmatrix} + (1-SpO_2) \begin{bmatrix} \beta_{HHB,\lambda_1} \\ \cdot \\ \cdot \\ \beta_{HHB,\lambda_i} \end{bmatrix} \right] \quad (16)$$

Assuming, as described above, that the shallow penetration is dominated by arterial blood, and that, e.g., two wavelengths of light $\lambda_1$ and $\lambda_2$ are emitted by emitter 502, the absorption associated with the shallow penetration can be represented by the following equation:

$$\begin{bmatrix} A_{\lambda_1,s} \\ A_{\lambda_2,s} \end{bmatrix} = \begin{bmatrix} W_{dis,\lambda_1,s} \\ W_{dis,\lambda_2,s} \end{bmatrix} \cdot \left[ S_{SpO_2} \cdot \begin{bmatrix} \beta_{O_2HB,\lambda_1} \\ \beta_{O_2HB,\lambda_2} \end{bmatrix} + (1-S_{SpO_2}) \cdot \begin{bmatrix} \beta_{HHB,\lambda_1} \\ \beta_{HHB,\lambda_2} \end{bmatrix} \right] \quad (17)$$

where $A_{\lambda_1,s}$ and $A_{\lambda_2,s}$ can be calculated by processing equipment according to Eq. (15) above based on the emitted light and the light detected by detector 504, the value of $S_{SpO_2}$ is a known value obtained by pulse oximetry, user input, or other suitable methods, and $\beta_{O_2HB}$ and $\beta_{HHB}$ are known coefficients associated with the specific emitters being used. Accordingly, $W_{dis,\lambda_1,s}$ and $W_{dis,\lambda_2,s}$, which are distortion factors associated with the shallow penetration for the given wavelengths $\lambda_1$ and $\lambda_2$, respectively, may be solved for using conventional techniques for solving the linear algebra matrix described in Eq. (17) above. It is understood in the art that additional wavelengths of light may be used to solve for additional corresponding distortion factors.

As shown by the mean path lengths 514 and 516 in FIG. 5A, both the shallow and deep penetrations travel through the shallow layer 508 twice. Accordingly, both the shallow and deep penetration signals may be dominated by the scattering and absorbance variability in the shallow layers, such that the distortion factors associated with the deep penetration can be assumed to be roughly equal to the distortion factors associated with the shallow penetration. In light of this assumption, the difference between the deep penetration and shallow penetration signals can be correlated to the saturation of the tissue, $rSO_2$, as follows:

$$\begin{bmatrix} \Delta A_{\lambda_1,d-s} \\ \Delta A_{\lambda_2,d-s} \end{bmatrix} = \begin{bmatrix} W_{dis,\lambda_1,s} \\ W_{dis,\lambda_2,s} \end{bmatrix} \cdot \left[ RSO_2 \cdot \begin{bmatrix} \beta_{O_2HB,\lambda_1} \\ \beta_{O_2HB,\lambda_2} \end{bmatrix} + (1-RSO_2) \cdot \begin{bmatrix} \beta_{HHB,\lambda_1} \\ \beta_{HHB,\lambda_2} \end{bmatrix} \right] \quad (18)$$

Where, $\Delta A_{\lambda_1,d-s}$ and $\Delta A_{\lambda_2,d-s}$ can be calculated by processing equipment based on the light detected by detectors 504 and 506, $W_{dis,\lambda_1,s}$ and $W_{dis,\lambda_2,s}$ are known based on solving the linear algebra matrix described in Eq. (17) above, and $\beta_{O_2HB}$ and $\beta_{HBB}$ are known coefficients associated with the specific emitters being used. Since there are two equations and only one unknown, $rSO_2$, the system of equations described by Eq. (18) is an overdetermined system. Accordingly, the system can be solved for $rSO_2$ using conventional techniques for solving overdetermined systems.

While two wavelengths of light have been used here for illustrative purposes, it can be understood that additional wavelengths of light may be used to further improve the accuracy of the calculation of $rSO_2$. For example, if three wavelengths of light, $\lambda_1$, $\lambda_2$, and $\lambda_3$, were emitted by light source 502, equation 16 could be expanded as follows:

$$\begin{bmatrix} A_{\lambda_1,s} \\ A_{\lambda_2,s} \\ A_{\lambda_3,s} \end{bmatrix} = \begin{bmatrix} W_{dis,\lambda_1,s} \\ W_{dis,\lambda_2,s} \\ W_{dis,\lambda_3,s} \end{bmatrix} \cdot \left[ S_{SpO_2} \cdot \begin{bmatrix} \beta_{O_2HB,\lambda_1} \\ \beta_{O_2HB,\lambda_2} \\ \beta_{O_2HB,\lambda_3} \end{bmatrix} + (1-S_{SpO_2}) \cdot \begin{bmatrix} \beta_{HHB,\lambda_1} \\ \beta_{HHB,\lambda_2} \\ \beta_{HHB,\lambda_3} \end{bmatrix} \right] \quad (19)$$

where $A_{\lambda_1,s}$, $A_{\lambda_2,s}$, and $A_{\lambda_3,s}$ can be calculated by processing equipment as described above, the value of $S_{SpO_2}$ is a known value as described above, $\beta_{O_2HB}$ and $\beta_{HHB}$ are again known coefficients associated with the specific emitters being used, and $W_{dis,\lambda_{1,s}}$, $W_{dis,\lambda_{2,s}}$, and $W_{dis,\lambda_{3,s}}$ may again be solved for using conventional linear algebra techniques. Having solved for the three distortion factors associated with the three wavelengths of light, Eq. (18) could then similarly be expanded as follows:

$$\begin{bmatrix} \Delta A_{\lambda_1,d-s} \\ \Delta A_{\lambda_2,d-s} \\ \Delta A_{\lambda_3,d-s} \end{bmatrix} = \begin{bmatrix} W_{dis,\lambda_{1,s}} \\ W_{dis,\lambda_{2,s}} \\ W_{dis,\lambda_{3,s}} \end{bmatrix} \cdot \begin{bmatrix} RSO_2 \cdot \begin{bmatrix} \beta_{O_2HB,\lambda_1} \\ \beta_{O_2HB,\lambda_2} \\ \beta_{O_2HB,\lambda_3} \end{bmatrix} + (1 - RSO_2) \cdot \begin{bmatrix} \beta_{HHB,\lambda_1} \\ \beta_{HHB,\lambda_2} \\ \beta_{HHB,\lambda_3} \end{bmatrix} \end{bmatrix} \quad (20)$$

The system of equations described by Eq. (20) could be solved for $rSO_2$ using conventional techniques for solving overdetermined systems, as described above with respect to Eq. (18). It will be understood that in some embodiments, four, five, six, or more wavelengths of light may be utilized, and Eqs. (17) and (18) can be similarly expanded and solved accordingly. The embodiments described above for calculating $rSO_2$ are only illustrative embodiments, and any suitable modifications may be made by those skilled in the art in accordance with the present disclosure.

In some embodiments, the value of one or more distortion factors may be updated. In some arrangements, one or more distortion factors may be updated by performing any of the calculations for determining distortion factors consistent with the present disclosure at predetermined intervals. Any physiological parameters calculated based on the distortion factors may accordingly be updated at the same predetermined intervals. In some arrangements, one or more distortion factors may be updated whenever a predetermined change in a given physiological parameter occurs. For example, the processing equipment may be configured to re-calculate one or more distortion factors whenever the arterial oxygen saturation value SpO2 changes by a certain percent or other value. Any physiological parameters calculated based on the distortion factors could accordingly be re-calculated once the distortion factors are recalculated. For example, local perfusion, cardiac output, stroke volume, $rSO_2$, any other suitable parameter, or any combination thereof calculated based on distortion factors may be re-calculated as the distortion factors are updated. In some embodiments, the re-calculated distortion factors may be used in subsequent calculations of physiological parameters.

In some embodiments, the value of one or more distortion factors can be monitored to determine physiological information. For example, the processing equipment may be configured to calculate and/or display a value indicative of changes in the distortion factor or factors as the distortion factor or factors are updated. In some embodiments, the value indicative of changes in the distortion factor or factors may be monitored in order to provide an alarm if the change is too large. For example, the change in the distortion factor or factors may be compared to one or more thresholds and an alarm may be generated based on the comparison (e.g., when the change in the distortion factor or factors crosses a threshold). The alarm may be an audible alarm, a visual alarm, or a combination thereof.

In some embodiments, the value indicative of change may be evaluated by the processing equipment according to conventional statistical methods to determine confidence information regarding the accuracy of the physiological signal or components thereof. For example, conventional statistical methods may determine when there is excessive variability in the distortion factors. Increased variability of the distortion factors may correlate to decreased confidence in the accuracy of the physiological signal received, or components thereof. Conversely, decreased variability in the distortion factors may correlate to increased confidence in the accuracy of the physiological signal received or components thereof. Accordingly, the processing equipment may be configured to display any standard statistical measurement of the distortion factors and/or corresponding values indicative of the confidence level in the physiological signal. In some embodiments, the values indicative of confidence level may be monitored in order to provide an alarm if the values are too low. For example, the confidence level may be compared to one or more thresholds and an alarm may be generated based on the comparison (e.g., when the confidence level crosses a threshold). The alarm may be an audible alarm, a visual alarm, or a combination thereof.

As is evident from the present disclosure, the system may be described more generally in terms of determining values indicative of oxygen saturation based on assumptions, determining distortion factors based on additional assumptions, and determining physiological information based on the distortion factors. For example, as described above, $SpO_2$ may be determined based on simplified assumptions regarding the path length of emitted light and the change in concentration of arterial blood and a relevant physiological signal. The simplified assumptions imply that these components do not factor into the calculation because they cancel out of the relevant equations. Then, it is assumed that these simplified assumptions are not accurate, and this assumption allows us to relate the calculated $SpO_2$ value to distortion factors that capture the variability of the components previously assumed to not impact $SpO_2$ and the relevant physiological signals. The distortion factors can then be determined based on the calculated $SpO_2$ value and the relevant physiological signals. Since these distortion factors capture this variability, they can be used to determine the same or other physiological information that is affected by this same variability.

Figure 6:
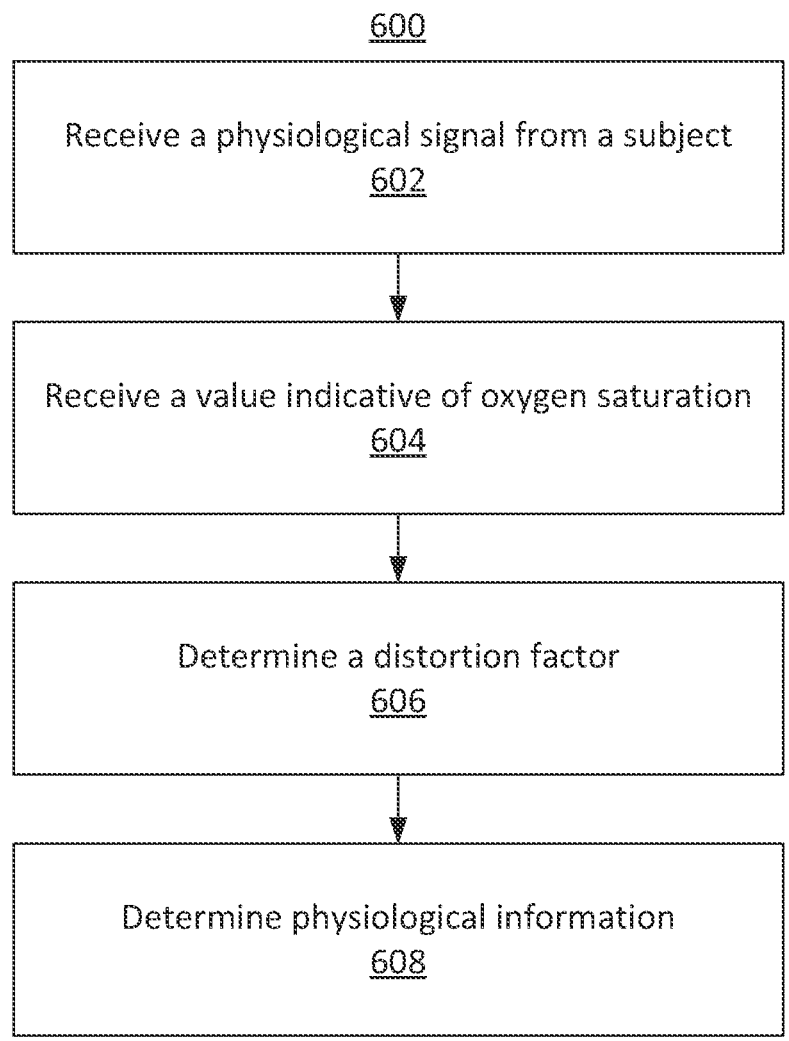
FIG. 6 shows an illustrative flow diagram including steps for determining physiological information in accordance with some embodiments of the present disclosure.

FIG. 6 shows an illustrative flow diagram 600 including steps for determining physiological information in accordance with some embodiments of the present disclosure.

Step 602 includes receiving a physiological signal from a subject. In some embodiments, the physiological signal may include a first component corresponding to a first wavelength of light and a second component corresponding to a second wavelength of light. In some embodiments, the physiological signal may include a first component corresponding to a first wavelength of light detected at a first depth, a second component corresponding to a second wavelength of light detected at the first depth, a third component corresponding to the first wavelength of light detected at a second depth, and a fourth component corresponding to the second wavelength of light detected at the second depth. In some embodiments, the physiological signal may include a PPG signal. In some embodiments, the physiological signal may be detected by detector 140 of FIG. 1. In some embodiments, the physiological signal may include detector current waveform 214 of FIG. 2. It will be understood that the received physiological signals may include signals received at a detector such as detector 140 of FIG. 1, signals received by a monitor such as monitor 104 of FIG. 1, signals received at backend processing such as back end processing circuitry 170 of FIG. 1, signals received by detectors 504 and/or 506 of FIGS. 5A and 5B, any other suitable signals, or any combination thereof.

In an example, a pulse oximeter may provide a light signal to a subject. The light signal may include time-multiplexed red and IR light pulses. The light may interact with a subject and be partially attenuated. In some embodiments, the attenuated light signal may be detected using a photodetector, which may generate a current signal that corresponds to the intensity of detected light. In some embodiments, the attenuated light signal may be detected using two photodetectors, which may generate current signals that correspond to the intensity of light detected at two locations.

Step 604 includes receiving a value indicative of oxygen saturation. In some embodiments, the value indicative of oxygen saturation may be computed by the back end processing circuitry 170 and received and stored into memory 174. In some embodiments, the value indicative of oxygen saturation may be received from a separate device via communications interface 190. For example, the separate device may be configured to have the components of physiological monitoring system 310. In some embodiments the value indicative of oxygen saturation may be received from a hospital information system or other coupled network via communications interface 190. In some embodiments, the value indicative of oxygen saturation may be received via user interface 180 from user input 182. The value indicative of oxygen saturation may be any suitable value that is indicative of oxygen saturation. For example, the value indicative of oxygen saturation may be an approximation of arterial oxygen saturation such as a ratio, a percentage, or any other suitable value. In some embodiments, the value indicative of oxygen saturation may be an $SpO_2$ value calculated from Eqs. (7)-(8) or from any related or otherwise equivalent expressions. In some embodiments, the value indicative of oxygen saturation may be a ratio R calculated from Eqs. (6a) and/or (6b) or from any related or otherwise equivalent expressions.

Step 606 includes determining a distortion factor. The distortion factor may correspond to and/or be unique to any of the wavelengths of light that comprise the physiological signal received. The distortion factor may be determined based on components of the physiological signal and the value indicative of oxygen saturation. In some embodiments, where the physiological signal is comprised of two wavelengths of light or more, two or more corresponding distortion factors may be determined. In some embodiments, three, four, or more distortion factors may be determined to correspond with the components of the physiological signal. In some embodiments, the distortion factor or factors may be determined by relating the value indicative of oxygen saturation to absorption or change in absorption. For example, the distortion factor or factors may be determined based on any of Eqs. (10), (11), (17), and (19).

Step 608 includes determining physiological information. The physiological information may be determined based on any of the distortion factors determined in step 606. The physiological information may include physiological parameters such as measures of arterial oxygen saturation, regional tissue oxygen saturation, local perfusion, stroke volume, cardiac output, any other suitable parameter, or any combination thereof. The physiological information may also include confidence information regarding the physiological signal. In some embodiments, a measure of regional tissue oxygen saturation may be determined based on two or more distortion factors according to one of Eqs. (18), (20), or any other suitable expressions. In some embodiments, a measure of local perfusion may be determined based on one or more distortion factors according to Eq. (12) or any other suitable expression. In some embodiments, stroke volume and/or cardiac output may be determined based on one or more distortion factors according to Eqs. (13), (14), or any other suitable expression. In some embodiments, confidence information regarding the physiological signal may be determined based on statistical analysis of values indicative of change in one or more of the distortion factors.

It will be understood that any of the aforementioned steps of flow diagram 600 may be repeated as desired. In some embodiments, any of steps 602, 604, 606, and 608 may be repeated at a predetermined interval in time. For example, the physiological signal may be received and updated continuously or periodically, the value indicative of oxygen saturation may be updated and received accordingly, and in turn, the distortion factors and physiological parameters may be re-calculated at these predetermined intervals. In some embodiments, any of steps 602, 604, 606, and 608 may be repeated when any physiological parameter exhibits a predetermined change or crosses a threshold value. For example, the distortion factors may be re-calculated whenever the value indicative of oxygen saturation changes by a predetermined amount or whenever the value indicative of oxygen saturation reaches a predetermined threshold.

It will be understood that the aforementioned steps of flow diagram 600 are exemplary and that in some implementations, steps may be added, removed, omitted, repeated, reordered, modified in any other suitable way, or any combination thereof. It will also be understood that the aforementioned mathematical expressions are merely exemplary and that any suitable values indicative of oxygen saturation, distortion factors, and other terms may be used.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A system for operating a physiological monitor, the system comprising:
    an input configured for receiving physiological signals, the physiological signals comprising a first physiological signal and a second, subsequent physiological signal, the first physiological signal and the second, subsequent physiological signal each comprising a first component corresponding to a first wavelength of light and a second component corresponding to a second wavelength of light; and
    one or more processors configured to perform operations comprising:
        receiving a value indicative of oxygen saturation;
        determining a distortion factor corresponding to one of the first and second wavelengths of light based on the first component of the received first physiological signal, the second component of the received first physiological signal, and the value indicative of oxygen saturation; and
        determining physiological information using the distortion factor and the second, subsequent physiological signal.

2. The system of claim 1, wherein determining the physiological information comprises:
   determining an AC component of the second, subsequent physiological signal;
   determining a baseline component of the second, subsequent physiological signal; and
   determining a value indicative of perfusion using the AC component, the baseline component, and the distortion factor.

3. The system of claim 2, wherein determining the value indicative of perfusion comprises determining the value indicative of perfusion using the following expression:

$$\frac{AC\ component}{baseline\ component} * \frac{1}{distortion\ factor}.$$

4. The system of claim 1, wherein the first component and the second component correspond to tissue at a first depth, wherein the second, subsequent physiological signal further comprises a third component corresponding to the first wavelength of light and a fourth component corresponding to the second wavelength of light, wherein the third component and the fourth component correspond to tissue at a second depth; wherein determining the physiological information comprises determining regional oxygen saturation using the first component, the second component, the third component, the fourth component, and the distortion factor.

5. The system of claim 4, wherein determining regional oxygen saturation comprise determining the regional oxygen saturation using an equation of the form:

$$\begin{bmatrix} \Delta A_{\lambda_1,d-s} \\ \Delta A_{\lambda_2,d-s} \end{bmatrix} = \begin{bmatrix} W_{dis,\lambda_1,s} \\ W_{dis,\lambda_2,s} \end{bmatrix} \cdot \left[ RSO_2 \cdot \begin{bmatrix} \beta_{O_2HB,\lambda_1} \\ \beta_{O_2HB,\lambda_2} \end{bmatrix} + (1-RSO_2) \cdot \begin{bmatrix} \beta_{HHB,\lambda_1} \\ \beta_{HHB,\lambda_2} \end{bmatrix} \right].$$

6. The system of claim 1, wherein the one or more processors are further configured to perform operations comprising determining a value indicative of changes in the distortion factor over time, wherein the physiological information comprises confidence information associated with the physiological signal.

7. The system of claim 1, wherein the one or more processors are further configured to perform operations comprising:
   determining a value indicative of changes in the distortion factor over time;
   comparing the value indicative of changes to a threshold; and
   generating an alert based on the comparison.

8. The system of claim 1, wherein the distortion factor comprises a first distortion factor corresponding to the first wavelength of light, wherein the one or more processors are further configured to perform operations comprising:
   determining a second distortion factor corresponding to the second wavelength of light based on the first component of the received first physiological signal, the second component of the received first physiological signal, and the value indicative of oxygen saturation, wherein determining the physiological information comprises determining the physiological information using the first distortion factor and the second distortion factor.

9. The system of claim 8, wherein the first physiological signal comprises a third component corresponding to a third wavelength of light, wherein the one or more processors are further configured to perform operations comprising:
   determining a third distortion factor corresponding to the third wavelength of light based on the first component of the received first physiological signal, the second component of the received first physiological signal, the third component of the received first physiological signal, and the value indicative of oxygen saturation, wherein determining the physiological information comprises determining the physiological information using the first distortion factor, the second distortion factor, and the third distortion factor.

10. The system of claim 1, wherein the physiological information comprises cardiac output information.

11. The system of claim 1, wherein the physiological information comprises stroke volume information.

12. The system of claim 1, wherein the value indicative of oxygen saturation comprises a ratio of oxygenated hemoglobin and total hemoglobin.

\* \* \* \* \*